(12) United States Patent
Rokicki

(10) Patent No.: US 8,377,237 B2
(45) Date of Patent: Feb. 19, 2013

(54) METHOD FOR SURFACE INCLUSIONS DETECTION IN NITINOL WHICH ARE PRIMARY CORROSION AND FATIGUE INITIATION SITES AND INDICATORS OF OVERALL QUALITY OF NITINOL MATERIAL

(76) Inventor: Ryszard Rokicki, Emmaus, PA (US)

(*) Notice: Subject to any disclaimer, the term of this patent is extended or adjusted under 35 U.S.C. 154(b) by 296 days.

(21) Appl. No.: 12/660,904

(22) Filed: Mar. 5, 2010

(65) Prior Publication Data

US 2010/0274077 A1 Oct. 28, 2010

Related U.S. Application Data

(60) Provisional application No. 61/214,380, filed on Apr. 23, 2009.

(51) Int. Cl.
| | | |
|---|---|---|
| C22F 1/10 | (2006.01) | |
| A61F 2/01 | (2006.01) | |
| A61F 2/82 | (2006.01) | |
| A61M 25/00 | (2006.01) | |
| A61B 17/03 | (2006.01) | |
| A61B 17/04 | (2006.01) | |

(52) U.S. Cl. ...... 148/402; 623/1.13; 623/1.15; 604/264; 606/200; 606/228; 606/219

(58) Field of Classification Search .......... 148/426, 148/402; 623/1.15, 1.13; 604/264; 606/200, 606/228, 219
See application file for complete search history.

(56) References Cited

U.S. PATENT DOCUMENTS

| | | | | |
|---|---|---|---|---|
| 5,080,584 | A * | 1/1992 | Karabin | 433/20 |
| 5,986,169 | A * | 11/1999 | Gjunter | 424/422 |
| 6,450,975 | B1 * | 9/2002 | Brennan et al. | 600/585 |
| 6,488,701 | B1 * | 12/2002 | Nolting et al. | 623/1.13 |
| 6,596,132 | B1 * | 7/2003 | Rasmussen et al. | 204/192.15 |
| 2003/0187497 | A1 * | 10/2003 | Boylan et al. | 623/1.15 |

OTHER PUBLICATIONS

Renata de Castro Martins, Maria Guiomar A. Bahia, Vicente T.L. Buono, Belo Horizonte, The effect of sodium hypochlorite on the surface characteristics and fatigue resistance of ProFile nickel-titanium instruments, Oral Surgery, Oral Medicine, Oral Pathology, Oral Radiology, and Endodontology, vol. 102, Issue 4, Oct. 2006, pp. e99-e105, ISSN.*
FDA Citizen Petition 2009-P-0362 filed by Ryszard Rokicki on Jul. 29, 2009 Request that FDA Issue an Order Mandating Inspection of every peripheral stent, cardiovascular stent, heart valve and IVC filter composed of Nitinol for Intermetallic Inclusions before sterilization. Ryszard Rokicki "Detecting Nitinol Surface Inclusions" Medical Device & Diagnostic Industry, Feb. 2010, p. 44-48, Canon Communication LLC Publication, Los Angeles, Ca.

* cited by examiner

*Primary Examiner* — Jessee R. Roe
(74) *Attorney, Agent, or Firm* — Sanford J. Piltch

(57) ABSTRACT

The method for surface inclusions detection in wrought and finished Nitinol products by immersing them in aqueous solution of 1% to 12%, and preferably 6%, sodium hypochlorite at room temperature of around 25° C. for specific period of time, preferably 15 minutes while checking for black flocculent precipitate developing on the surface indicating the presence of an inclusion. The presence of black flocculent precipitate indicates surface inclusions and lack of homogeneousness of material.

14 Claims, No Drawings

METHOD FOR SURFACE INCLUSIONS DETECTION IN NITINOL WHICH ARE PRIMARY CORROSION AND FATIGUE INITIATION SITES AND INDICATORS OF OVERALL QUALITY OF NITINOL MATERIAL

BACKGROUND OF THE INVENTION

The present invention relates to the field of chemical testing of intermetallic materials, more specifically for testing intermetallic compound of nickel and titanium commonly known as Nitinol for surface inclusions and lack of homogeneousness by immersing it in aqueous solution of sodium hypochlorite (NaClO) and checking for black flocculent precipitate developing on the particular surface site.

The site or sites where this black flocculent precipitate start to develop is the place of surface inclusion and give evidence of lack of homogeneousness of Nitinol material, which is sign of inferiority and should be the base for rejection of such raw material or finished product.

The surface inclusions are causing the maximum stress during bending-rotation and flexing especially peripheral stents and lead to their fracture. Also inclusions are sources by themselves of sites were corrosion starts to dissolve matrix materials releasing nickel ions harmful to living cells surrounding particular implantable device.

The Nitinol inclusions can be classified in two ways: by its origin and by its chemical composition. The classification by origin giving us two kinds of inclusions: native which originate during production of bulk material and another one foreign introduce during finishing operations.

The native inclusions are randomly distributed through whole volume of material and finding them on the surface is the excellent indicator of quality of the bulk of material. In contrast foreign inclusions are strictly surface phenomenon introduced to the surface during finishing operations as: glass-bead, sand or aluminum oxide blasting, heat treatment, mechanical polishing, lapping, laser cutting, drawing, electro discharge machining etc.

The classification by chemical composition is more complicated. Taking under consideration the very small size of inclusions the chemical analysis is often difficult and very often leads to error. Those inclusions could be broadly classified as carbides (TiC), oxides ($Ti_4N_2O_x$, $TiO_2$) or intermetallic precipitates ($Ni_4Ti_3$).

It is widely recognized that carbides are created during (VIM) vacuum induction melting from carbon crucibles used in this process. On another hand oxides are originate in bigger amount and in larger particles size during (VAM) vacuum arc melting. The third process which claims four to ten times lower carbon content due to use of water cooled crucibles is (EBM) electron beam melting.

But regardless of all of the Nitinol production methods mentioned above, none of them is perfect and in the present time it isn't possible to produce 100% inclusions free, homogeneous Nitinol.

Till now the only way to check up the Nitinol surface for inclusions were microscopic and instrumental methods as: scanning electron microscope (SEM) with energy dispersive X-ray (EDX) spectrometry, atomic force microscopy (AFM), transmission electron microscopy (TEM) X-ray diffraction, Auger spectrometer with back-scatter electron detector (BSE).

All of those above mentioned techniques are very expensive, time consuming, demanding highly trained operators and by this they are excellent techniques for scientific research or limited industrial inspections, but unpractical for large scale production inspections.

Because of this the present invention which is very simple, inexpensive, very effective (almost 100%), doesn't require expensive instrumentation and highly trained operators and can be applied to raw materials as well to finished products are perfectly suited for mass inspections.

In the event of positive test results of raw material intended for production, material can be rejected before even starting expensive manufacturing processes and by this money and time can be saved.

The post production test of finished products can eliminate defected products (which have avoided detection during raw material testing, because inclusions were not present on the surface during initial test and appear on the surface as a results of production operations: removing excess material by mechanical, chemical or electrochemical processes and revealing inclusions from the bulk of material or by introducing externally new inclusions to the surface of finished products as a result of manufacturing operations as laser cutting, sand blasting, drawing etc.

By applying post production testing lot of very serious (fracture of endodontic rotary file for example) and even death threatening problems (as for example fracture of carotid stent or neurovascular coil used to treat brain aneurysm) could be avoided.

BRIEF SUMMARY OF THE INVENTION

The present invention relates to method for surface inclusions detection in wrought and finished Nitinol products. The overlooked surface inclusion in Nitinol could lead to very undesirable consequences as fractures, enhanced corrosion behavior, lower or diminished bio, and hemocompatibility of medical implantable devices and medical and dental instruments.

DESCRIPTION OF THE INVENTION

In recent years usage of Nitinol almost equiatomic binary intermetallic compound of nickel and titanium has been steadily growing. The main field in which Nitinol are finding more and more applications are medical and dental devices markets. The Nitinol medical devices can be divided into two main group, one consist of implantable as for example peripheral stents, cardiovascular luminal shields, heart valves etc. Another one includes tools and instruments used during medical procedures as stone and blood clots retrievers, vena cava filters, endoscopes, etc. The dental devices are endodontic rotary files, orthodontic archwires, etc.

The main reason for this growing usage of Nitinol arise from remarkable combination of mechanical (pseudoplasticity and shape memory) and biocompatible properties. The unusual mechanical properties of Nitinol are due to its ability to undergo reversible change between two crystals structure.

The good biocompatibility originates from its chemical composition. The very high content of titanium is responsible for the spontaneous creation of very rich titanium oxide, which is also present on commercially pure titanium and another titanium containing alloys.

The quest to develop almost totally homogenous, inclusions free Nitinol, with improved fatigue and corrosion resistance properties continues. Among the new approaches to achieve this goal are: smart anodization, acidic and basic chemical etching, heat treatment in different gaseous atmospheres, ion implantation, cryogenic treatment, electropolishing and the latest proposed magnetoelectropolishing process.

But all of the above mentioned methods with their claimed and actual working properties are destined to failure how long finished Nitinol products will not be surface inclusions free and homogenous.

It is well documented that about 80% of crack initiation in Nitinol stents are triggered by visible surface inclusions. The best evidence about importance of this problem is fact that Nitinol producers are offering now Extra Low Inclusion Nitinol (EUROFLEX, Nitinol SE 508 ELI).

The main inclusions identified in Nitinol are titanium carbides (TiC), which are introduced to Nitinol mainly during vacuum induction melting (VIM) and originate from carbon crucibles used during the melting process. Another group of inclusions are oxidized intermetallics as $Ti_2NiO$ and oxides as $TiO_2$ introduced in larger amount during vacuum arc remelting (VAR) process.

Despite that Nitinol surface inclusions are not a trivial matter, and cause many problems as corrosion, Ni leaching, fatigue initiation sites, local martensitic transformation and stress concentration points they haven't been studied too extensively till now.

The main way to check the Nitinol surface for inclusions till now are instrumental observation techniques as: transmission electron microscopy (TEM), Auger electron spectroscopy (AES) with back-scatter electron (BSC) detector, scanning electron microscopy (SEM) with energy dispersive X-ray (EDX) spectrometry, atomic force microscopy (AFM) and X-ray diffraction. All of those techniques are very expensive, time consuming, demanding very highly trained operators, sophisticated equipment and despite this are not very effective and practical in mass inspection on industrial scale.

The present invention overcomes the problems mentioned above by providing a totally novel, inexpensive, more practical and almost 100% reliable testing method, which is not restricted by size or shape of tested Nitinol material for surface inclusions.

To my knowledge the present invention of testing Nitinol for surface inclusions by using sodium hypochlorite (NaClO) is totally new and never was employed or even mention in the prior art in this field.

As long as the interatomic bonds between Ni and Ti in Nitinol remain intact, the intermetallic compound will stay totally inert when exposed to aqueous solution of sodium hypochlorite (NaClO). But when those bonds are broken by precipitated inclusions the Nitinol becomes very prone to corrosion by sodium hypochlorite.

The mechanism of this corrosion arises from aggressiveness of NaClO toward Ni. When Ni metal is exposed to NaClO chemical reaction starts immediately and follows till all Ni is dissolved or NaClO is used according to reaction:

$$2Ni + 3NaClO + 3H_2O \rightarrow 2Ni(OH)_3\downarrow + 3NaCl$$

The visual sign of this reaction is black flocculent precipitate of $Ni(OH)_3\downarrow$.

When homogenous surface inclusions free Nitinol is exposed to NaClO nothing happens. The spontaneously (by ambient atmosphere) or artificially (by electropolishing or magnetoelectropolishing process for example) created $TiO_2$ efficiently protects Nitinol against corrosion.

Even when Nitinol is broken when submerged in NaClO and broken surfaces don't contain inclusions corrosion doesn't start, because freshly broken inclusion free surfaces are immediately oxidized by very powerful oxidizer (NaClO) to $TiO_2$ which prevents corrosion.

But in the case when Nitinol posses surface inclusions corrosion starts almost immediately. Characteristic black flocculent oozes from the reaction site with inseparable effervescence of oxygen gas $O_2\uparrow$ according to the following reaction:

$$9NaClO + 2NiTi + 7H_2O \rightarrow 2Ni(OH)_3\downarrow + 2Ti(OH)_4\downarrow + 9NaCl + O_2\uparrow$$

It is essential to mention that the dissolving Ni can come from two sources: from the matrix surrendering inclusion which is enriched in Ni during the process of creation of inclusion which drains Ti elements to creates inclusion as TiC or from inclusion itself which is enriched in Ni as for example intermetallic inclusions of $Ni_4Ti_3$, $Ni_3Ti$ created for example during wire drawing operation. But doesn't matter from where $Ni(OH)_3$ originates both cases indicate presence of inclusions and lack of Nitinol homogeneousness.

Titanium hydroxide $Ti(OH)_4$ (white precipitate) which originates alongside when corrosion progresses is masked by black color of $Ni(OH)_3\downarrow$, but also can be visible by naked eye. Those two distinguished (by color) precipitates originated in the places of inclusions in the presence of NaClO are evidence that in this case Nitinol corrodes as Ti and Ni separately and not as intermetallic compound.

The usefulness of the present invention is shown in following examples. The examples used represent only possible embodiments of the test procedure described here and should not in any way imply any restriction to the condition used here.

EXAMPLES

Example 1

Checking unfinished Nitinol endodontic rotary files for surface inclusions brand I.

The investigated files consisted of one piece of Nitinol rod with finished (grounded) working cutting end and unfinished holding second end. The finished end was shiny and bright. The holding unfinished end was black. The black color indicated that rod underwent drawing operation which left oxidized black surface.

Prior to inclusion testing black drawing oxide was removed by etching. The etching solution consisted of $HF:HNO_3:H_2O$ in 1:5:20 volume ratio.

Thirty six Nitinol files were tested. Files were submerged vertically in 6% aqueous solution of sodium hypochlorite in glass vessel in room temperature around 25° C. for period of 24 hours. Submerged files were visually observed nonstop during the first two hours. After first two hours files were checked every hour.

Results: In first 15 minutes corrosion reaction started on the unfinished surfaces of six separate files. Black flocculent started to ooze from the corrosion reaction sites. After 24 hours no more files started to develop corrosion. Among six files which started to corrode in first 15 minutes of exposure four of them ceased to corrode and two still underwent corrosion when checked after 24 hours.

None of thirty six files tested developed corrosion on grinded working (cutting) end during 24 hours.

Example 2

Checking ready to use commercial Nitinol endodontic rotary files for surface inclusions brand II.

Fifty four files were tested. They were partially (only working ground end) submerged in 6% NaClO in glass container for two hours in room temperature around 25° C. for two hours and constantly observed.

Results: Four files started to corrode (each one in only one localized place) in first 15 minutes of submersion. Black flocculent oozed from corrosion places. After two hours of submersion three files ceased to corrode and fourth one underwent further corrosion.

Example 3

Electropolished Nitinol wire was submerged in 6% NaClO in glass tube in room temperature around 25° C. Almost immediately wire started to corrode in one place, black flocculent started to develop in corrosion site. Bubble of oxygen was observed departing upward from corrosion site. After 1 hour corrosion progressed from the same sites.

The invention claimed is:

1. The method for surface inclusion detection in unfinished and finished products of compounds containing substantially equal parts of nickel and titanium comprising the steps of immersing said unfinished or finished products in an aqueous solution of sodium hypochlorite (NaClO) of between 1% and 12% by weight for a predetermined period of time at room temperature of around 25° C. and checking said unfinished or finished products for black flocculent precipitate which will ooze from one or more sites on the surface of said unfinished or finished products indicating the presence of one or more surface inclusions.

2. The method for surface inclusion detection in unfinished and finished products of compounds containing substantially equal parts of nickel and titanium of claim 1, wherein said aqueous solution of sodium hypochlorite of between 1% and 12% by weight is approximately 6% by weight.

3. The method for surface inclusion detection in unfinished and finished products of compounds containing substantially equal parts of nickel and titanium of claim 1, wherein said predetermined time period for immersing the unfinished or finished products in an aqueous solution of sodium hypochlorite of between 1% and 12% by weight is preferred to be 15 minutes.

4. The method for surface inclusion detection in unfinished and finished products of compounds containing substantially equal parts of nickel and titanium] of claim 1, wherein said finished products of compounds containing substantially equal parts of nickel and titanium are selected from the group consisting of medical implantable devices, medical devices and instruments, and dental devices and instruments.

5. The method for surface inclusion detection in unfinished and finished products of compounds containing substantially equal parts of nickel and titanium of claim 4, wherein said finished products consisting of medical implantable devices are selected from the group consisting of bare metal stents, stent grafts, polymer covered stents, aneurysm coils, heart valves, arterial septal defect occlusion devices and orthopedic devices.

6. The method for surface inclusion detection in unfinished and finished products of compounds containing substantially equal parts of nickel and titanium of claim 4, wherein said finished products consisting of medical devices and instruments are selected from the group consisting of angioplasty guidewires, catheters, sutures, staples, stones and blood clots retrievers, vena cava filters, Mitek sutures anchors, cutting blades, endoscopes.

7. The method for surface inclusion detection in unfinished and finished products of compounds containing substantially equal parts of nickel and titanium of claim 4, wherein said finished products consisting of dental devices and instruments are selected from the group consisting of endodontic rotary files, endodontic hand files, orthodontic archwires.

8. The method for surface inclusion detection in unfinished and finished products of compounds containing substantially equal parts of nickel and titanium of claim 1, wherein said unfinished products of compounds containing substantially equal parts of nickel and titanium are selected from the group consisting of nickel/titanium compounds, composite nickel/titanium compounds, porous nickel/titanium compounds and thin film nickel/titanium compounds.

9. The method for surface inclusion detection in unfinished and finished products of compounds containing substantially equal parts of nickel and titanium of claim 8, wherein said unfinished products consisting of composite nickel/titanium compounds are produced by vacuum induction melting (VIM), vacuum arc melting (VAR), electron beam melting (EBM) and induction skull melting (ISM).

10. The method for surface inclusion detection in unfinished and finished products of compounds containing substantially equal parts of nickel and titanium of claim 8, wherein said unfinished products consisting of composite nickel/titanium compounds surround or encapsulate other metals as platinum, tantalum, gold or alloy of 90% platinum-10% nickel.

11. The method for surface inclusion detection in unfinished and finished products of compounds containing substantially equal parts of nickel and titanium of claim 8, wherein said unfinished products consisting of porous nickel/titanium compounds possess a porosity of 8%-90% and are defined by networks of interconnected passageways extending throughout material, which exhibits permeability permitting complete migration of fluid material throughout said network.

12. The method for surface inclusion detection in unfinished and finished products of compounds containing substantially equal parts of nickel and titanium of claim 11, wherein said porous nickel/titanium compounds are of an independent material or in the form of a coating covering another material.

13. The method for surface inclusion detection in unfinished and finished products of compounds containing substantially equal parts of nickel and titanium of claim 8, wherein said unfinished products consisting of thin film nickel/titanium compounds are fabricated by vacuum deposition technologies or rf magnetron sputtering.

14. The method for surface inclusion detection in unfinished and finished products of compounds containing substantially equal parts of nickel and titanium of claim 13, wherein said thin film nickel/titanium compounds are of an independent material or in the form of a coating covering another material.

* * * * *